(12) United States Patent
Ohki

(10) Patent No.: US 8,013,603 B2
(45) Date of Patent: Sep. 6, 2011

(54) NMR-DETECTING CELL, NMR-MEASURING METHOD, AND NMR-MEASURING APPARATUS

(75) Inventor: Shinya Ohki, Nomi (JP)

(73) Assignee: Japan Advanced Institute of Science and Technology, Ishikawa (JP)

(*) Notice: Subject to any disclaimer, the term of this patent is extended or adjusted under 35 U.S.C. 154(b) by 709 days.

(21) Appl. No.: 12/067,365

(22) PCT Filed: Sep. 20, 2006

(86) PCT No.: PCT/JP2006/318650
§ 371 (c)(1),
(2), (4) Date: Mar. 19, 2008

(87) PCT Pub. No.: WO2007/034842
PCT Pub. Date: Mar. 29, 2007

(65) Prior Publication Data
US 2010/0264919 A1    Oct. 21, 2010

(30) Foreign Application Priority Data
Sep. 20, 2005    (JP) .................................. 2005-272887

(51) Int. Cl.
*G01V 3/00* (2006.01)
(52) U.S. Cl. ........................................ 324/309; 324/307
(58) Field of Classification Search .......... 324/300–322; 600/407–445
See application file for complete search history.

(56) References Cited

U.S. PATENT DOCUMENTS

| | | | |
|---|---|---|---|
| 5,508,384 A * | 4/1996 | Murphy et al. ............... | 530/324 |
| 5,867,026 A * | 2/1999 | Haner .......................... | 324/321 |
| 5,887,026 A | 3/1999 | Arai | |
| 6,177,798 B1 * | 1/2001 | Haner et al. .................. | 324/321 |
| 6,396,274 B1 * | 5/2002 | Commens et al. ............ | 324/321 |
| 6,456,078 B1 * | 9/2002 | Iwata ............................ | 324/321 |
| 6,700,379 B2 * | 3/2004 | Peck et al. .................... | 324/321 |
| 6,867,594 B2 * | 3/2005 | Fey et al. ...................... | 324/321 |
| 7,068,034 B2 * | 6/2006 | de Swiet ....................... | 324/321 |
| 7,145,340 B2 * | 12/2006 | Rindlisbacher et al. ...... | 324/321 |
| 7,338,809 B2 * | 3/2008 | Yokoi ........................... | 436/176 |

FOREIGN PATENT DOCUMENTS

| | | |
|---|---|---|
| JP | 11-507441 A | 8/1999 |
| JP | 2002-139558 A | 5/2002 |
| JP | 2003-139831 | 5/2003 |
| JP | 2004-093187 A | 3/2004 |
| JP | 2004-138545 | 5/2004 |

OTHER PUBLICATIONS

Notification of Transmittal of Translation of the International Preliminary Report on Patentability dated Apr. 3, 2008 with English translation of the International Preliminary Report on Patentability and Written Opinion of the International Searching Authority for PCT/JP2006/318650.

* cited by examiner

*Primary Examiner* — Brij B Shrivastav
(74) *Attorney, Agent, or Firm* — Kilyk & Bowersox, P.L.L.C.

(57) ABSTRACT

An object of the present invention is to provide an effective method for measuring by NMR in real time, an NMR-detecting cell for measurement of NMR, and an NMR-measuring apparatus, and
specifically, there has been found out a method for measuring NMR wherein a measurement sample is immobilized in a medium in an NMR-detecting cell that is an NMR detection part within an NMR-measuring magnet, and then measured by solution NMR in real time under the condition that the external environment around the immobilized measurement sample is consecutively changing.

17 Claims, 6 Drawing Sheets

NMR-DETECTING CELL, NMR-MEASURING METHOD, AND NMR-MEASURING APPARATUS

This application is a National Stage Application of PCT/JP2006/318650, filed Sep. 20, 2006, which claims priority to JP 2005-272887 filed Sep. 20, 2005.

TECHNICAL FIELD

The present invention relates to an effective measuring method using solution NMR.

Further, the present application claims priority from Japanese Patent Application No. 2005-272887 incorporated herein by reference.

BACKGROUND ART

The present program on post-genome discovery focuses on the elucidation of the stereochemical conformation of an individual biomolecule, and will direct itself on more and more important studies on the interactions with the other biomolecules and the accompanying conformational changes. Those studies require efficient techniques, such as NMR measurement, to develop.

However, it is difficult for conventional NMR measurement technique that a thousand kinds of low molecular compounds for example are screened for substances interacting with a protein in interest. In such case, a procedure is presumed that the protein is mixed with ten kinds of low molecular compounds to prepare a measurement sample solution, which is then subjected to primary screening. However, the procedure needs preparing hundred sample solutions and making hundred turns of NMR measurement/analysis, and hence it takes a lot of time and a large amount of labor consumed to carry out this procedure repeatedly.

An automatic measurement sample changer can be applied to an NMR-measuring apparatus to improve the efficiency of the procedure, but it saves only a manual work for measurement sample exchange, and does not at all contribute to save the amount of the protein to use, the job for measurement sample preparation, and measurement time to consume.

The method for measuring solution NMR includes gel phase NMR analysis and liquid chromatography NMR analysis, but they have insufficient capacity to trace the conformational change of a protein, particularly the midterm process toward the folding of the protein.

The technique for measuring a measurement sample using an NMR method precedent to the present invention includes a technique wherein a filler is provided in the sample pathway inside an NMR probe to absorb the sample and then the absorbed sample is subject to NMR measurement (Patent document 1). However, the filler is provided in the sample pathway to concentrate the sample and prevent diffusion of the sample, and a screening method is not disclosed at all.

The technique for measuring a target polymeric substance using an NMR method precedent to the present invention includes a technique wherein the target polymeric substance is immobilized on a solid phase to make NMR measurement (Patent document 2). According to this technique, the target polymeric substance is immobilized on a solid phase under a liquid environment to make NMR measurement, or the immobilized substance is further supplied with a candidate compound to make NMR measurement about the result of their interaction. However, this system can not determine the process of their interaction by NMR, and can not conduct high throughput screening wherein many candidate compounds are consecutively supplied to measure. It is far from sufficient to effectively measure a sample.

[Patent document 1] Japanese Patent Application Laid-Open No. 2002-139558

[Patent document 2] Japanese Patent Application Laid-Open No. 2004-138545

DISCLOSURE OF THE INVENTION

Problems to be Solved by the Invention

An object of the present invention is to provide an NMR-measuring method which allows effective NMR measuring in real time the action of change in external environment around a measurement sample; and an NMR-detecting cell and an NMR apparatus facilitating the same method.

Means for Solving the Problems

The present invention comprises mainly an NMR-measuring method wherein a measurement sample is immobilized in a medium in an NMR-detecting cell that is an NMR measurement part within an NMR-measuring magnet and then measured in real time by solution NMR under a condition of consecutive change in the external environment around the immobilized measurement sample.

Namely, the present invention comprises:

1. A method for solution NMR-measuring, wherein a measurement sample is immobilized in a medium in an NMR-detecting cell within an NMR-measuring magnet and then measured by solution NMR under the condition that the external environment around the immobilized measurement sample is consecutively changing.
2. The method for solution NMR-measuring according to the preceding Item 1, wherein the measurement sample is immobilized by adsorbing on a solid-phase carrier.
3. The method for solution NMR-measuring according to the preceding Item 1 or 2, wherein the change in the external environment is a change in the medium in which the immobilized measurement sample is present.
4. The method for solution NMR-measuring according to any one of the preceding Items 1 to 3, wherein the change in the external environment is mediated by a solution-introducing pipe and a solution-discharging pipe of the NMR-detecting cell within the NMR-measuring magnet.
5. An NMR-detecting cell for a solution NMR apparatus comprising:
1) A solution-introducing pipe extending outside the NMR-measuring magnet;
2) A solution-discharging pipe extending outside the NMR-measuring magnet; and
3) An analytical column which can be connected to the solution-introducing pipe and the solution-discharging pipe and further filled with a solid-phase carrier.
6. The NMR-detecting cell for a solution NMR apparatus according to the preceding Item 5, wherein the analytical column is provided with filters on the introducing side and/or on the discharging side.
7. A solution NMR apparatus comprising the NMR-detecting cell for a solution NMR apparatus according to the preceding Item 5 or 6.
8. A solution NMR apparatus comprising:
1) An analytical column filled with a solid-phase carrier capable of immobilizing a measurement sample in a medium;

2) A solution-introducing pipe capable of supplying a solution for changing the external environment around the immobilized measurement sample or a candidate interactive substance; and 3) A solution-discharging pipe capable of discharging the solution or the candidate interactive substance.

9. The solution NMR apparatus according to the preceding Item 7 or 8, wherein the analytical column is detachable.

10. The solution NMR apparatus according to any one of the preceding Items 7 to 9, wherein the analytical column is provided with filters on the introducing side and/or on the discharging side.

11. A method for carrying out solution NMR measurement in real time comprising:

1) A step for immobilizing a measurement sample on a solid-phase carrier in an analytical column in an NMR-detecting cell;

2) A step for supplying a solution containing external environment-changing factors through a solution-introducing pipe in order to change consecutively the external environment around the immobilized measurement sample; and 3) A step for solution NMR-measuring of the measurement sample during the step 2) for supplying to change the external environment.

12. The method according to the preceding Item 11, wherein the measurement sample is a protein and further the midterm process toward the folding of the protein is traced by consecutive changing the external environment around the immobilized measurement sample.

13. A method for high throughput screening candidate interactive substances comprising:

1) A step for immobilizing a measurement sample on a solid-phase carrier in an analytical column in an NMR-detecting cell;

2) A step for supplying the immobilized measurement sample with a candidate interactive substance through a solution-introducing pipe;

3) A step for solution NMR measurement of the interaction between the measurement sample and the candidate interactive substance;

4) A step for supplying a solvent capable of dissociating only the association between the measurement sample and the candidate interactive substance through the solution-introducing pipe to release the candidate interactive substance from the measurement sample, which is then discharged from the NMR-detecting cell through a solution-discharging pipe; and 5) A step for repeating the steps 2) to 4).

More concretely, the present invention comprises:

1. A method for solution NMR-measuring, wherein a measurement sample is immobilized in a medium in an NMR-detecting cell within an NMR measuring magnet and then measured by solution NMR under the condition that the external environment around the immobilized measurement sample is consecutively changing.

2. The method for solution NMR-measuring according to the preceding Item 1, wherein the measurement sample is immobilized by adsorbing on a solid-phase carrier.

3. The method for solution NMR-measuring according to the preceding Item 1 or 2, wherein the change in the external environment is a change in the medium in which the immobilized measurement sample is present.

4. The method for solution NMR-measuring according to the preceding Item 3, wherein the change in the external environment is mediated by a solution-introducing pipe and a solution-discharging pipe of the NMR-detecting cell within the NMR-measuring magnet.

5. The method for solution NMR-measuring according to any one of the preceding Items 1 to 4, wherein the external environment-changing factors are addition/no addition or change in concentration of a coexisting substance, addition/no addition or change in concentration of an amphipathic reagent, the change in pH of a solvent, change in salt concentration, addition/no addition or change in concentration of a modification agent, or a combination of any two or more of these factors.

6. The method for solution NMR-measuring according to any one of the preceding Items 1 to 5, wherein the coexisting substance is a candidate interactive substance.

7. The method for solution NMR-measuring according to any one of the preceding Items 1 to 6, wherein the measurement sample is immobilized in an analytical column of the NMR-detecting cell by a method selected from followings:

1) A method wherein the measurement sample, which has ability to bind with the solid-phase carrier and holds a linker having a sufficiently high degree of freedom, is bound with the solid-phase carrier via the linker;

2) A method wherein the measurement sample is chemically bound with the solid-phase carrier; and 3) A method wherein the measurement sample is trapped by the solid-phase carrier having a high degree of freedom.

8. The method for solution NMR-measuring according to the preceding Item 7, wherein the solid-phase carrier having a high degree of freedom is dextran or a network structure of polymer gel 9. The method for solution NMR-measuring according to any one of the preceding Items 1 to 8, wherein the method is one for making solution NMR measurement in real time and comprises:

1) A step for immobilizing a measurement sample on a solid-phase carrier in an analytical column in an NMR-detecting cell;

2) A step for supplying a solution containing external environment-changing factors through a solution-introducing pipe in order to change consecutively the external environment around the immobilized measurement sample; and 3) A step for solution NMR-measuring of the measurement sample during the step 2) for supplying to change the external environment.

10. The method according to any one of the preceding Items 1 to 9, wherein the measurement sample is a protein and further the midterm process toward the folding of the protein is traced by consecutive changing the external environment around the immobilized measurement sample.

11. The method according to any one of the preceding Items 1 to 9, wherein the method is a method for high through-put screening candidate interactive substances and comprises:

1) A step for immobilizing a measurement sample on a solid-phase carrier in an analytical column in an NMR-detecting cell;

2) A step for supplying the immobilized measurement sample with a candidate interactive substance through a solution-introducing pipe;

3) A step for solution NMR measurement of the interaction between the measurement sample and the candidate interactive substance;

4) A step for supplying a solvent capable of dissociating only the association between the measurement sample and the candidate interactive substance through the solution-introducing pipe to release the candidate interactive substance from the measurement sample, which is then discharged from the NMR-detecting cell through a solution-discharging pipe; and 5) A step for repeating the steps 2) to 4).

12. The method according to any one of the preceding Items to 9, wherein the external environment around the immobilized measurement sample is consecutively changed to orientate the molecule sequences of the measurement sample toward one direction.

13. An NMR-detecting cell for a solution NMR apparatus comprising:
   1) A solution-introducing pipe extending outside the NMR measuring magnet;
   2) A solution-discharging pipe extending outside the NMR measuring magnet; and
   3) An analytical column which can be connected to the solution-introducing pipe and the solution-discharging pipe and further filled with a solid-phase carrier.

14. The NMR-detecting cell for a solution NMR apparatus according to the preceding Item 13, wherein the analytical column is provided with filters on the introducing side and/or on the discharging side.

15. A solution NMR apparatus comprising the NMR-detecting cell for a solution NMR apparatus according to the preceding Item 13 or 14.

16. A solution NMR apparatus comprising:
   1) An analytical column filled with a solid-phase carrier capable of immobilizing a measurement sample in a medium;
   2) A solution-introducing pipe capable of supplying a solution for changing the external environment around the immobilized measurement sample, or a candidate interactive substance; and
   3) A solution-discharging pipe capable of discharging the solution or the candidate interactive substance.

17. The solution NMR apparatus according to the preceding Item 15 or 16, wherein the analytical column is detachable.

18. The solution NMR apparatus according to any one of the preceding Items 15 to 17, wherein the analytical column is provided with filters on the introducing side and/or on the discharging side.

Effect of the Invention

The NMR measuring method of the present invention has an advantage that it can consecutively change an external environment around a measurement sample, it can effectively analyze the process of the interaction between the measurement sample and a candidate interactive substance, and further it can trace in real time the conformational change of a protein.

DESCRIPTION OF THE PREFERRED EMBODIMENT

The present invention is an NMR-measuring method which comprises an improved NMR-detecting cell in an NMR detection part (NMR probe) within an NMR-measuring magnet of a solution NMR-measuring apparatus.

In the NMR measuring method in the present invention, any method for use in conventional solution NMR can be used. Particularly, a high-magnetic-field NMR-measuring apparatus provided with a cryogenic probe is thought to give sufficient measurement sensitivity. Taking into consideration the interchangeability with a conventional NMR-detecting cell for an NMR-measuring apparatus, the NMR-detecting cell for the solution NMR-measuring apparatus of the present invention has a solution-introducing pipe, an analytical column, and a solution-discharging pipe which are each detachable and preferably take the form of being inserted from the top of an NMR magnetic field.

NMR-Detecting Cell

The NMR-detecting cell in the present invention comprises:
1) A solution-introducing pipe extending outside the NMR measuring magnet (101);
2) A solution-discharging pipe extending outside the NMR measuring magnet (103); and
3) An analytical column which can be connected to both the solution-introducing pipe and the solution-discharging pipe and further filled with a solid-phase carrier (102) (FIG. 1). The analytical column is filled with a solid-phase carrier (204); the outlet end of the solution-introducing pipe is inserted inside the inlet end of the analytical column; and the inlet end of the solution-discharging pipe is inserted inside the outlet end of the analytical column (FIG. 2). The solution-introducing pipe and the solution-discharging pipe are sealed up from their respective inserted ends in the analytical column by an appropriate method, and are each fixed by a liquid leak-proofing packing.

Preferably, the inlet side (the introducing side) and/or the outlet side (the discharging side) of the analytical column may be provided with filters (205) to prevent the measurement sample from flowing out into the solution-discharging pipe or diffusing into the solution-introducing pipe. The NMR-detecting cell may have a plurality of solution-introducing and solution-discharging pipes to simultaneously supply the measurement sample with a plurality of candidate interactive substances or to simultaneously change a plurality of external environmental factors.

Further, the NMR-detecting cell may be identical to a conventional NMR-detecting cell used in a solution NMR-measuring apparatus in respect of cell material and length and inner diameter of a solution-introducing pipe, a solution-discharging pipe, and an analytical column. Therefore, it has interchangeability with the conventional NMR cell used in a solution NMR-measuring apparatus. Within the NMR-measuring magnet of a solution NMR-measuring apparatus, the conventional NMR-detecting cell can be replaced by the NMR-detecting cell of the present invention. Concretely, joint parts for connecting the analytical column, the solution-introducing pipe and/or the solution-discharging pipe can be made to have a screw type so that the analytical column gets detachable.

Measurement Sample

The measurement sample of the present invention includes protein, polypeptide, nucleic acid, saccharide, glycoprotein, glycolipid, fatty acid, their derivatives, the covalent products, and the complexes of the aforementioned substance. The polypeptide is preferably used to consist of 40 or more and 1,000 or less of amino acid residues. The nucleic acid, saccharide, glycoprotein, glycolipid, and fatty acid are preferable to have their respective molecular weights of 1,000 or more and 100,000 or less. Concretely, they include, but not limited to, a naturally occurring protein and a protein with one or more amino acid residues added to the N-terminal or C-terminal of the naturally occurring protein. One or more amino acids may be deleted from, substituted in, or added to the amino acid sequence of the protein or polypeptide.

Labeling of the measurement sample may be introduced by labeling the whole molecule with stable isotopes such as $^{13}C$ and $^{15}N$, or with specifically stable isotopes to the distinct site.

Medium

The medium of the present invention is generally an aqueous solution to contact with the measurement sample. Any aqueous solution may be used as long as it can be used for NMR measurement and is retentive of the conformation in the case where a protein is a measurement sample. Concretely, the aqueous solution includes, but not limited to, pure water, classical buffer solutions (such as glycine, acetic acid, phosphoric acid, cacosylic acid, and imidazole), Good buffer solutions (such as Tris, Bis-Tris, Mes, HEPES, and CHES), and the aforementioned solution containing protease inhibitors (such as AEBSF, leupeptin, EDTA, and pepstatin A), polyhydric compounds (such as saccharose, glycerol, and polyethylene glycol), an SH group protective agent, antioxidants (such as 2-mercaptoethanol, and dithiothreitol), surfactants (such as octylglucoside, dodecylmaltoside, CHAPS, and Triton X-100), a lipid (such as DPC, and DHPC), organic solvents (such as glycerol, propanol, TFE, and DMSO), and an aqueous solution containing these compounds labeled with stable isotopes.

External Environment

The external environment of the present invention means an environment around a measurement sample. The factor for changing the external environment of the present invention means the addition, no addition, or concentration change of a coexisting substance, the addition, no addition or concentration change of a modification agent, the addition, no addition, or concentration change of an amphipathic reagent, the pH change of a solvent, concentration change of salt, the change of a medium, or occurrence of a combination of any two or more of these factors. The coexisting substance is a candidate interactive substance to a measurement sample.

Candidate Interactive Substance

The candidate interactive substance of the present invention means a substance that has some interaction with the measurement sample. The interaction includes, but not limited to, covalent bond, hydrophobic bond, hydrogen bond, Van der Waals bond, and electrostatic bond with the measurement sample. The concrete example includes an interaction in which the substance acts as an agonist, an antagonist, a reverse agonist, an inhibitor, or a promoter in relation with the action of the measurement sample. The interaction also includes a bond reaction with the measurement sample, a synthesis reaction of a new compound, and a decomposition reaction of the measurement sample which are caused by the results of the above actions.

Solid-Phase Carrier

The solid-phase carrier of the present invention has no special limitations as long as solution NMR measurement can be performed, and includes a resin and inorganic compounds such as glass, ceramics, latex and metal (but limited to non-magnetic compounds). The solid phase may take any form as long as it can be used for solution NMR measurement, and is preferably a particle such as a bead. The resin includes, but not limited to, specific examples as follows: resins used for combinatorial chemistry [such as TentaGel, Polystyrene Resin, ArgoGel, 2-Chlorotrityl resin, Kaiser Oxime Resin, Phosphine Resin, Rink-amide Resin, Thiomethyl Resin, Merrifield Resin, Wang Resin (SIGMA, Aldrich, etc.)], zinc ion chelating resins [such as Chelating FF (Amersham, etc.)], glutathione-immobilizing resins [such as Glutathione Sepharose 4B, Glutathione Sepharose 4FF (Amersham), GST/bind resin (Novagen)], IgG antibody-immobilizing sepharose resins [such as Protein G Plus/Protein A-Agarose (Novagen), BPV-1 (AU1) Affinity Matrix, HA.11 Affinity Matrix, FLAG Affinity Matrix, 6-His Affinity Matrix, c-myc Affinity Matrix, Polyoma Virus Medium T Antigen Affinity Matrix (COVANCE), ANTI-FLAG M1 or M2 Affinity gel (Sigma-Aldrich)], an amylose resin [such as Amylose resin (Novagen)], streptactin binding resins [such as StrepTactin Sepharose, StrepTactin POROS (Sigma-Genosys)], streptavidin binding resins [Streptavidin-CPG (CPG), Streptavidin Sepharose High Performance (Amersham), SoftLink resin, TetraLink resin(Promega)], a calmodulin immobilizing resin [such as Calmodulin-affinity resin (Stratagene)], a chitin resin [such as Chitin resin (New England Biolabs)], a lectin binding resin [such as Lentil Lectin Sepharose 4B (Amersham)], a concanavalin A binding resin [such as ConA Sepharose 4B (Amersham)], an S-protein-immobilizing resin [such as S-Protein agarose (Novagen)], nucleic acid-immobilizing resins [such as Poly(A) Sepharose 4B, Poly(U) Sepharose 4B, Poly(C) Type6 (Amersham)].

A particle size of solid phase carrier thus prepared may have one commonly adopted for a solid phase carrier.

The solid-phase carrier includes, in terms of the solid-phase carrier to a measurement sample, antibody to antigen, avidin or streptavidin to biotin, hormone (such as insulin) to hormone receptor (such as insulin receptor), and corresponding sugar chain to lectin.

Filling Method of Solid-Phase Carrier

The filling method of solid-phase carrier may be any method as long as it allows filling an analytical column with a solid-phase carrier.

For example, a tube is connected to the inlet end of an analytical column, and then supplied with a buffer solution containing the solid-phase carrier to introduce the carrier into the analytical column through the tube. The buffer solution in the analytical column is discharged from the outlet end of the column.

In the case where the measurement sample is a gel, it may be directly introduced into the analytical column filled with the solid-phase carrier. Further, the analytical column may be provided with a filter to prevent the gel measurement sample to flow out and/or a packing to prevent liquid leakage.

Immobilization Method of Measurement Sample

The immobilization of a measurement sample is to immobilize a protein or the like as the measurement sample on a solid-phase carrier through the use of chemical binding, affinity binding, or antigen-antibody reaction. The measurement sample is preferably immobilized on the aforementioned solid-phase carrier filled in the analytical column, allowing consecutive change of external environments around the measurement sample. Furthermore, following ways are possible to apply.

1) A measurement sample is furnished with a linker capable of binding to the solid-phase carrier and having a sufficient degree of freedom.

If the measurement sample is a peptide, a substance which is crosslinkable with the SH group of the peptide can be used as a linker. The linker is preferably a compound which has one end to react with the SH group and another end to react with any of OH group, COOH group and $NH_2$ group. Such a linker includes a dicarboxylic acid, an aminocarboxylic acid, a bis-maleimide compound, a bis-halocarbonyl compound, a halocarbonyl maleimide compound, dithiomaleimide, dithiocarboxylic acid, and maleimidocarboxylic acid. The spacer is not particularly limited as long as it can position between the measurement sample and the linker to regulate a distance between the measurement sample and the surface of the solid-phase carrier. One or a combination of plural substances selected from a polyoxyethylene, a polypeptide, a polysaccharide, albumin, and an antibody can be used as the spacer.

The recombinant of albumin or an antibody also can be used.
2) A measurement sample is chemically bound to a solid-phase carrier.

The measurement sample is chemically bound to the solid-phase carrier by the reactive group of the measurement sample which combines with a substituent group introduced on the surface of the solid-phase carrier. The reactive group is not limited to a specific kind as long as it is a functional group which is chemically capable of coupling with the reactive functional group of the solid-phase carrier as described above, and is preferably selected from an amino group, a carboxyl group, a hydroxyl group, a thiol group, an aldehyde group, an epoxy group, an alkyl haliode, a sylyl halide and the like appropriately depending on the reactive functional group of the solid-phase carrier. The chemical bond thus obtained is preferably an amide bond, an ester bond, a thioester bond, an ether bond, a thioether bond, an alkylamino bond, an imino bond, s sylylether bond, and the like, and particularly preferably an amide bond and a thioether bond. The reactive reagent to form the chemical bond may be appropriately selected depending on the bond.

3) A measurement sample is trapped by a solid-phase carrier having a high degree of freedom.

In the case where the solid phase carrier has a high degree of freedom, it can be used with no linker/spacer to carry out NMR measurement. However, the solid-phase carrier, when combined with the linker/spacer as described above to use, can give a better measurement result. The carrier having a high degree of freedom includes a liposome, a micelle, a protein polymer, and a polymer. It specifically includes a liposome, a recombinant albumin polymer, a latex particle, a polymer gel, particularly a polymer gel having a network structure, and a polysaccharide. The liposome is a particle composed of lipid artificial membrane which is made to have double layers of phospholipid, glycerolipid, cholesterol, and the like. It is prepared by applying generally known methods such as a surfactant removing method, a hydration method, an ultrasonication method, a reverse phase distillation method, a freeze-thawing method, an ethanol injection method, an extrusion method, and a high pressure emulsion method. The recombinant albumin, which is prepared by a genetic engineering, may be used and is not particularly limited. For example, the recombinant albumin which is prepared by using yeast as a host on the practical level is preferable to use. The atomization (polymerization) of albumin is well known. The polymer gel, which is made to have a network structure, can be prepared, for example, by atomizing a polymer obtained by polymerization of lactic acid and/or glycolic acid. Dextran as a polysaccharide is a suitable carrier, and can mediate amine coupling reaction to couple chemically a linker with a measurement sample compound.

Measuring Method

In the method for measuring NMR in the present invention, any method can be adopted as long as it is used conventionally for solution NMR-measuring. Concretely, the homonuclear multi-dimensional NMR measurement includes, but not limited to, COSY, TOCSY, NOESY, and ROESY, while the heteronuclear multi-dimensional NMR measurement includes, but not limited to, HSQC, HMQC, CH-COSY, CBCANH, CBCA(CO)NH, HNCO, HN(CA)CO, HNHA, H(CACO) NH, HCACO 15N-edited NOESY-HSQC, 13C-edited NOESY-HSQC, 13C/15N-edited HMQC-NOESY-HMQC, or 13C/13C-edited HMQC-NOESY-HMQC, 15N/15N-edited HSQC-NOESY-HSQC.

Solution NMR-Measuring Apparatus

The solution NMR-measuring apparatus of the present invention has a solid-phase carrier capable of immobilizing a measurement sample in a medium in an NMR-detecting cell which is an HMR detection part within an NMR measuring magnet, and has a means to allow consecutive change in the external environment around the immobilized measurement sample.

The solution NMR apparatus comprises:
1) An analytical column filled with a solid-phase carrier capable of immobilizing a measurement sample in a medium;
2) A solution-introducing pipe capable of supplying a solution for changing the external environment around the immobilized measurement sample or a candidate interactive substance; and
3) A solution-discharging pipe capable of discharging the solution or the candidate interactive substance.

Preferably, the apparatus comprises an NMR-detecting cell which has a plurality of solution-introducing and solution-discharging pipes or has the analytical column provided with filters on the introducing side and/or on the discharging side.

The conventional solution NMR-measuring apparatus can be converted to the solution NMR-measuring apparatus of the present invention by removing the NMR-detecting cell within the NMR-measuring magnet and then introducing the NMR-detecting cell of the present invention.

Embodiment of the Present Invention

According to following embodiments, the NMR-measuring method of the present invention can not only identify a substance interacting with a measurement sample, but also consecutively change the external environment around the measurement sample, allowing 1) tracing the midterm process of protein folding, 2) tracing the process of interaction between the measurement sample and an interactive substance, 3) releasing the immobilized measurement sample, 4) conducting high throughput screening for a candidate interactive substance interacting with the measurement sample, and 5) orientating the molecular sequence of the measurement sample in a definite direction. These are impossible to accomplish through the use of conventional solution NMR-measuring methods. Further, the NMR-detecting cell having a plurality of introducing and discharging pipes can be used to change simultaneously a plurality of factors for external environment, allowing conducting solution NMR measurement under external environments under which it is impossible to conducting measurement through conventional methods.

Furthermore, it is considered that in the case where the measurement sample, which is not a perfect aqueous solution, is used, SIM control using the sample (fine control to improve the magnetic homogeneity of an NMR apparatus necessary for high quality of NMR spectroscopy) is difficult. Thus, the same type of an aqueous solution is previously used to control SIM, and then the NMR-detecting cell filled with the measurement sample is applied, allowing exemption of SIM control necessary to conduct the measurement.

Non-linear measurement on an indirect observation axis side, DFT, and Hadamard transform can be used to shorten the measurement time, allowing monitoring a measurement sample in real time. In the method for identify NMR spectral signal, per se well-known and commonly used methods are used.

1) Measuring Method for Allowing Tracing Midterm Process of Protein Folding

The protein which is a measurement sample is immobilized on the solid-phase carrier in the analytical column of an NMR-detecting cell. Then, the immobilized measurement sample is supplied with a substance influencing the conformation of the protein such as a modification agent through the solution-introducing pipe. The concentration of the modification agent is little by little increased to change gradually the conformation of the measurement sample, thereby to measure the changing process in real time by NMR. Also, the introduction through the solution-introducing pipe can be stopped to measure. Furthermore, various modification agents can be supplied to the measurement sample to screen for an optimal environmental condition for folding the measurement sample. The solution containing the modification agent supplied is then discharged through the solution-discharging pipe outside the NMR-measuring magnet.

2) Measuring Method for Allowing Tracing Process of Interaction Between Measurement Sample and Interactive Substance The measurement sample is immobilized on the solid-phase carrier in the analytical column of an NMR-detecting cell. Then, the interactive substance interacting with the measurement sample is supplied with the immobilized measurement sample through the solution-introducing pipe. The process of change in conformation of the measurement sample, which is caused by coexistence of the measurement sample with the interactive substance, is measured in real time by NMR. Specifically, the interactive substance is consecutively supplied little by little to the measurement sample to cause a change, which is then measured in real time by NMR.

Furthermore, another interactive substance can be supplied with the measurement sample, which has interacted one interactive substance through the solution-introducing pipe to analyze substances causing two or more steps of interactions.

Furthermore, the site of the measurement sample is identified to bring a change in signal, allowing specifying the site of the measurement sample with which the interactive substance is coupled.

3) Measuring Method for Allowing Releasing Immobilized Measurement Sample

The measurement sample is immobilized on the solid-phase carrier in the analytical column of an NMR-detecting cell to make NMR measurement. Then, a solvent capable of releasing the measurement sample from the solid phase carrier is supplied with the immobilized measurement sample through the solution-introducing pipe. The measurement sample which is not immobilized is subjected to NMR measurement. By comparing both results of NMR measurements, it is possible to detect which site of the measurement sample contributes to the immobilization.

Therefore, a novel NMR measuring method can be carried out using a phenomenon that the immobilized measurement sample is not measurable while the released measurement sample becomes measurable.

4) High Throughput Screening for Candidate Interactive Substance Interacting with Measurement Sample The measurement sample is immobilized on the solid-phase carrier in the analytical column of an NMR-detecting cell. Then, the candidate interactive substance is supplied with the immobilized measurement sample through the solution-introducing pipe. The change or its process in conformation of the measurement sample, which is caused by coexistence of the measurement sample with the candidate interactive substance, is measured in real time by NMR. Then, a solvent for dissociating only the bond between the measurement sample and the candidate interactive substance is supplied through the solution-introducing pipe to dissociate the candidate interactive substance from the measurement sample, and further discharged outside the NMR-detecting cell through the solution-discharging pipe. Again, another candidate interactive substance is supplied through the solution-introducing pipe to measure by NMR. The processes as described above can be repeated to conduct high throughput screening for candidates interactive substances.

5) Measuring Method for Allowing Orientating Molecular Sequence of Measurement Sample in a Definite Direction The measurement sample is immobilized on the solid-phase carrier in the analytical column of an NMR-detecting cell. Then, the solution is supplied at varying flow rates to orientate the molecular sequence of the measurement sample in a definite direction, and the orientation is then measured by NMR.

EXAMPLE

The present invention will be described below in more detail in reference to Examples. The following Examples are intended to help in understanding the present invention, and do not limit the scope of the present invention.

Example 1

Preparation of NMR-Detecting Cell for Solution NMR Measurement Filled with Solid-Phase Carrier A tube was connected to the inlet end of an analytical column. The tube was supplied with a buffer containing a resin which is a solid-phase carrier to introduce the resin into the analytical column through the tube. Only the buffer in the analytical column was discharged from the outlet end of the analytical column. A commercially available resin capable of binding specifically to GST was selected to use.

Then, the outlet end of a solution-introducing pipe was inserted inside the inlet end of the analytical column filled with the resin, while the inlet end of a solution-discharging pipe was inserted inside the outlet end of the analytical column. The analytical column was provided with filters on the inlet side (introducing side) and the outlet side (discharging side). Further, the analytical column was provided with a packing on the inlet side (introducing side) to prevent liquid leakage.

Example 2

Measuring Method Using NMR-Detecting Cell for Solution NMR Measurement of the Present Invention The fused protein as measurement sample [GST(glutathione S transferase) was coupled with a signal transmission protein calmodulin through the mediation of a linker (LVPRGSAM-(GGGGS)$_4$-LEVLFQGPH:sequence number No. 1) to obtain the protein (GST/linker/calmodulin)] was introduced in the NMR-detecting cell for solution NMR measurement prepared in Example 1. Then, the cell was set within an NMR magnetic field to conduct solution NMR measurement under a condition of 25° C. and point number 1024.

$^1$H-$^{15}$N HSQC Measurement Result

The $^1$H signal in the amide group that was a main chain of the signal transmission protein calmodulin could be detected (Reference FIG. 3). Namely, the fused protein GST bound to the solid-phase carrier resin, while the signal transmission protein calmodulin was found in the liquid phase through the mediation of the linker. Further, the spectrum of the amide group that was a main chain of the signal transmission protein calmodulin could be very sensitivity detected.

$^1H$-$^{15}N$ HSQC Measurement Result

The $^1H$-$^{15}N$ signal in the amide group that was a main chain of the signal transmission protein calmodulin could be detected (Reference FIG. 4). Namely, the fused protein GST bound to the solid-phase carrier resin, while the signal transmission protein calmodulin was found in the liquid phase through the mediation of the linker. Further, the spectrum of the amide group that was a main chain of the signal transmission protein calmodulin could be detected.

The above results has revealed that, for example, a solvent is supplied through the introducing pipe to change consecutively the external environment around the measurement sample, allowing 1) tracing the midterm process of the folding of a protein, 2) tracing the process of interaction between a measurement sample and an interactive substance, 3) releasing an immobilized measurement sample, and 4) conducting high throughput screening for a candidate interactive substance interacting with the measurement sample.

INDUSTRIAL APPLICABILITY

The NMR measuring method of the present invention can change consecutively the external environment around a measurement sample to analyze effectively the process of interaction between the measurement sample and a candidate interactive substance, and further can trace the change in conformation of a protein in real time.

Explanation of Reference Numerals

Figure 1:
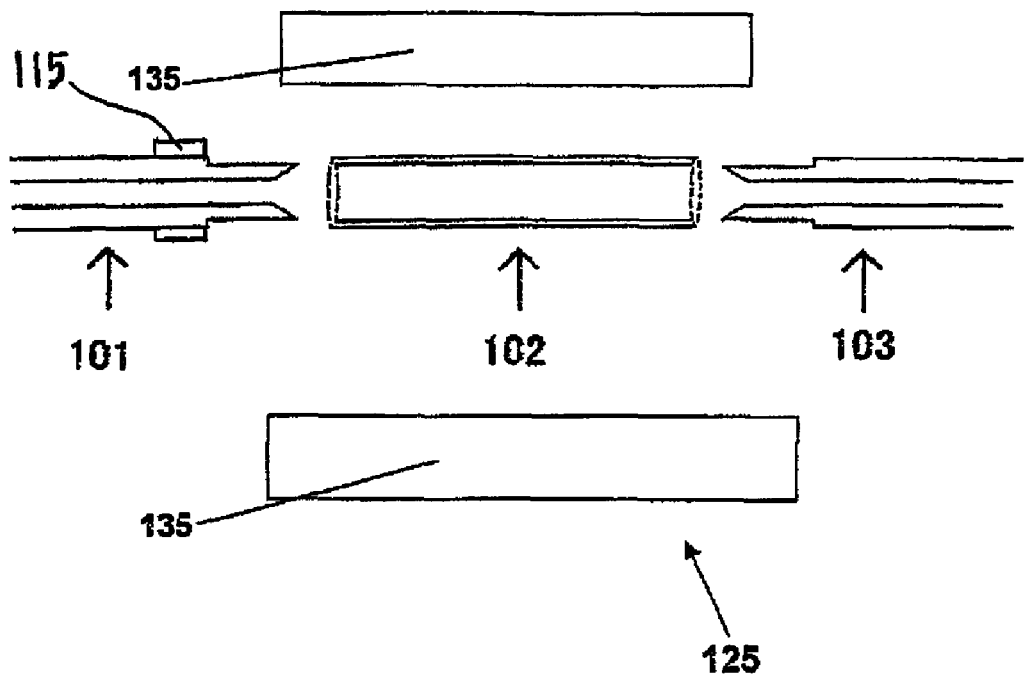
FIG. 1 is a schematic illustration of an NMR-detecting cell for a solution NMR apparatus.
Figure 2:
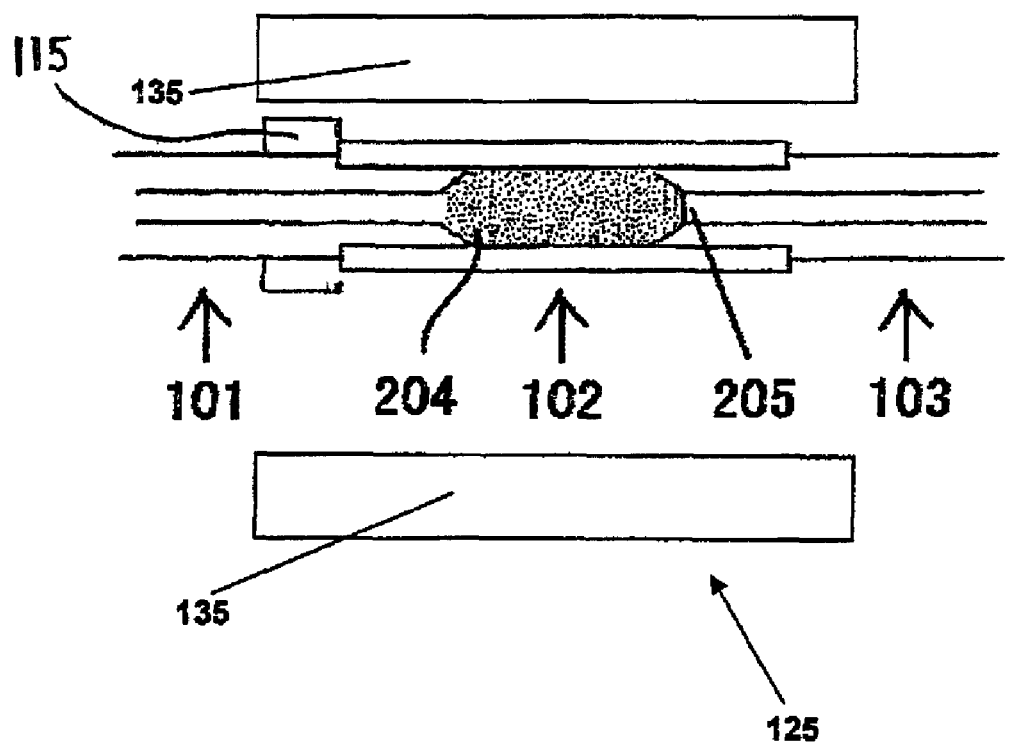
FIG. 2 is a schematic illustration of an NMR-detecting cell for a solution NMR apparatus, where the cell is filled with solid-phase carrier.
Figure 3:
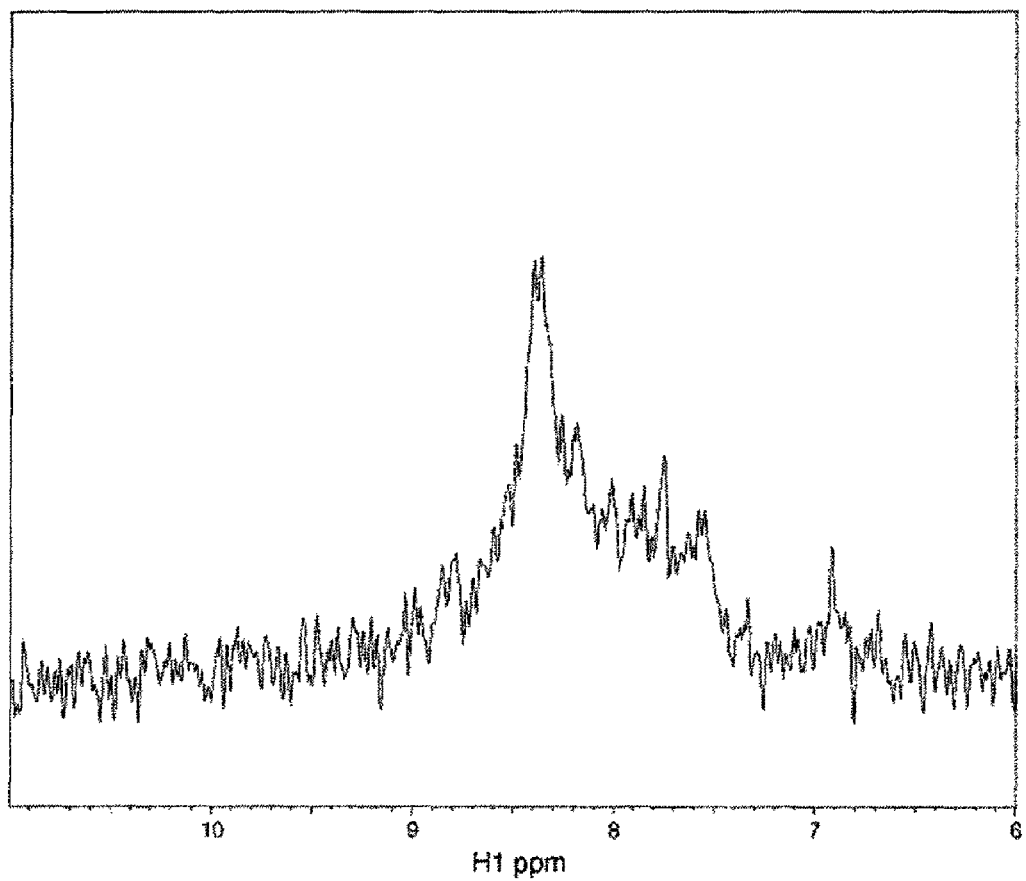
FIG. 3 shows the detection result of the $^1H$ signal of the signal transmission protein calmodulin.
Figure 4:
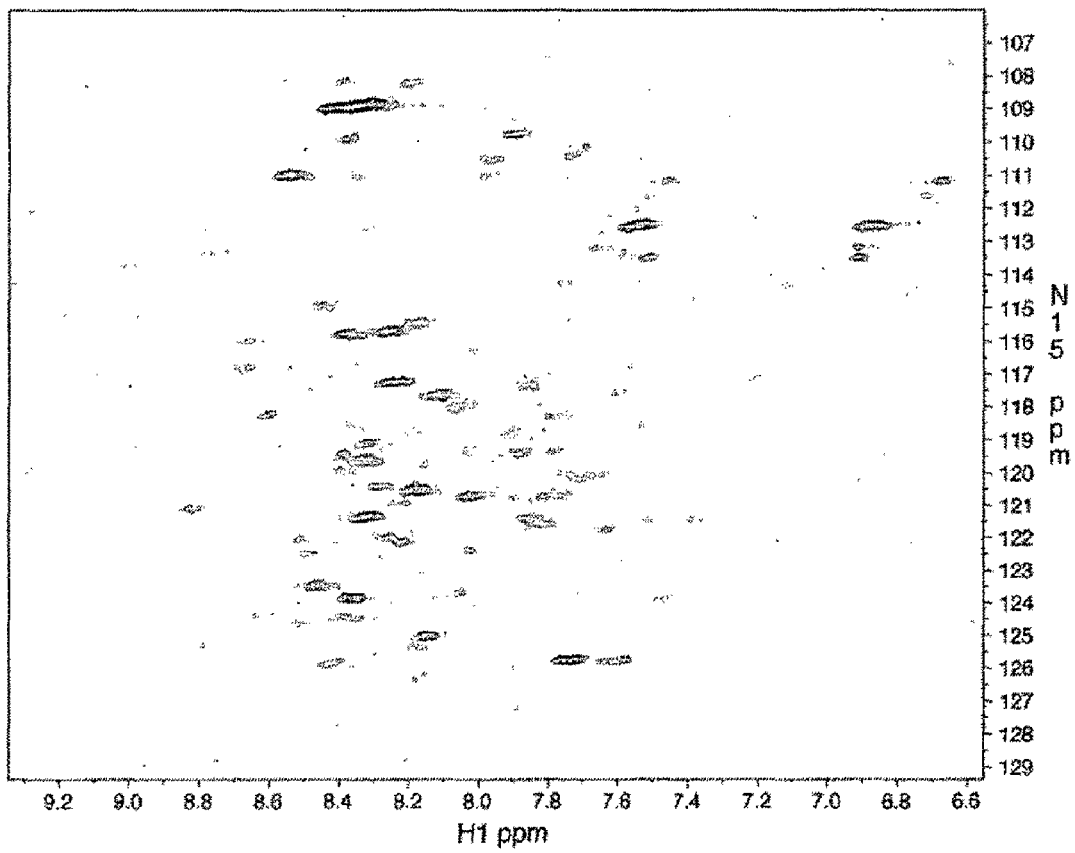
FIG. 4 shows the detection result of the $^1H$-$^{15}N$ signal of the signal transmission protein calmodulin.
Figure 5:
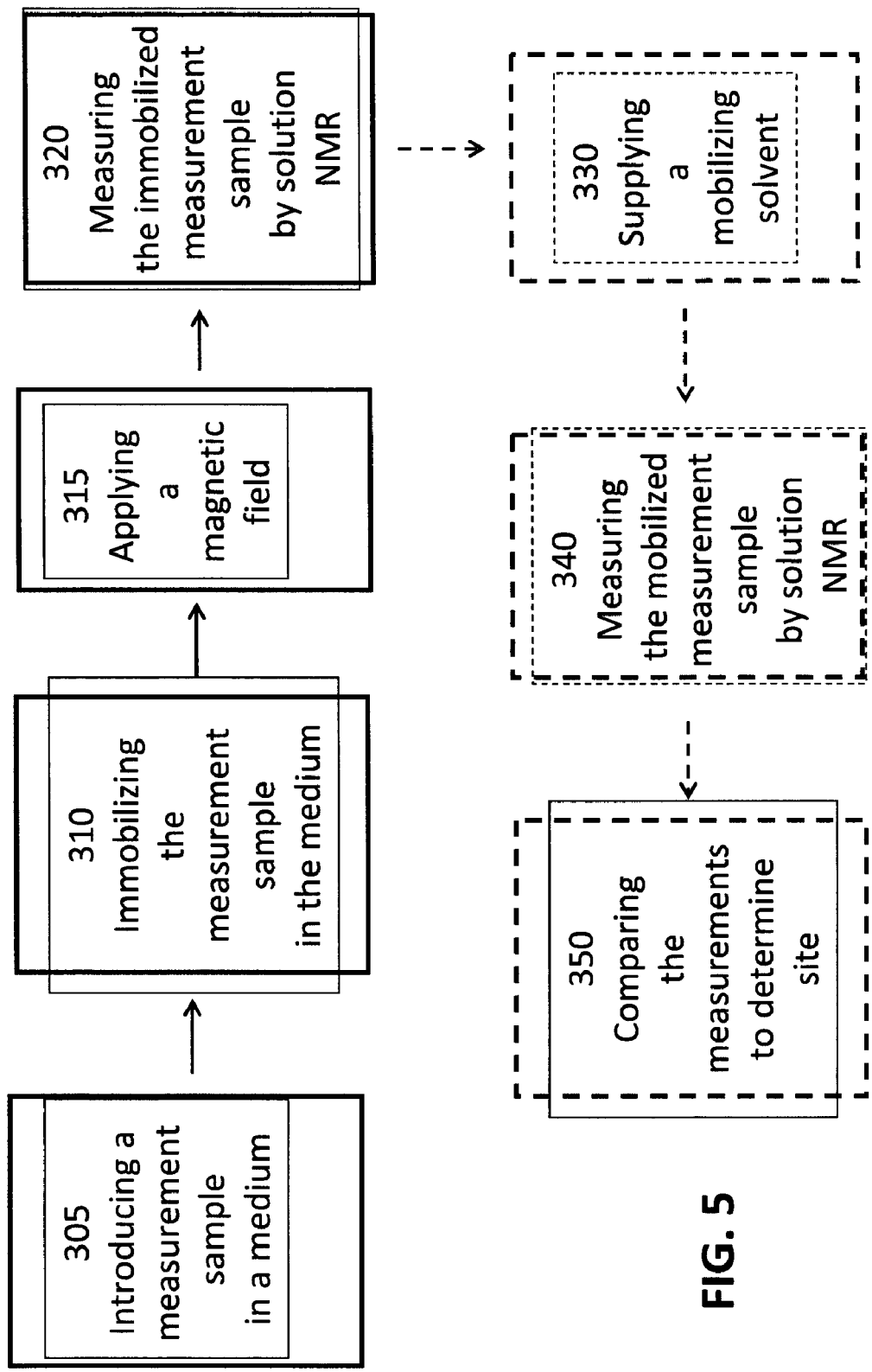
FIG. 5 is a diagram showing an example of various steps that can be performed in accordance with the methods of the present invention.
Figure 6:
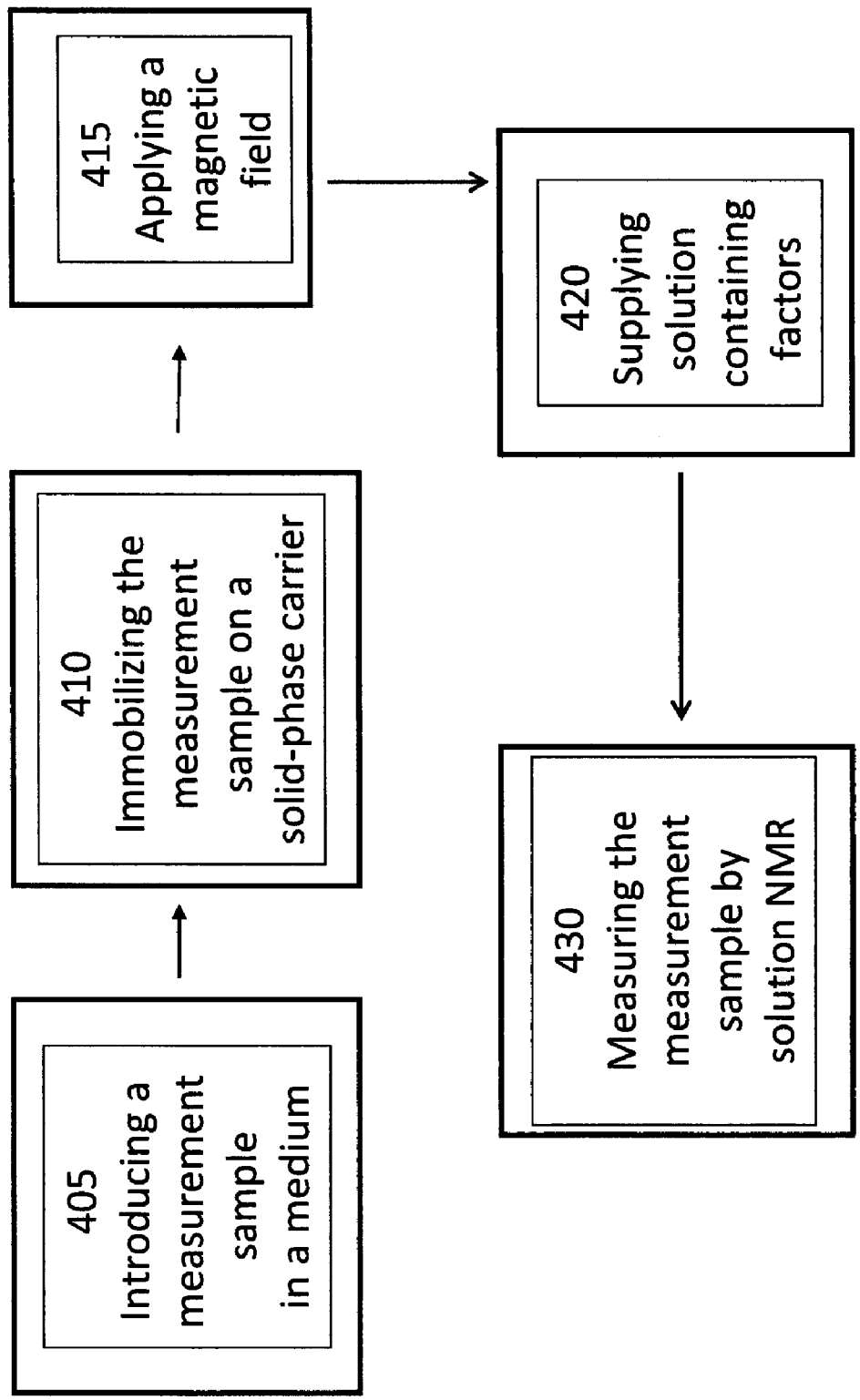
FIG. 6 is a diagram showing another example of various steps that can be performed in accordance with methods of the present invention.
Figure 7:
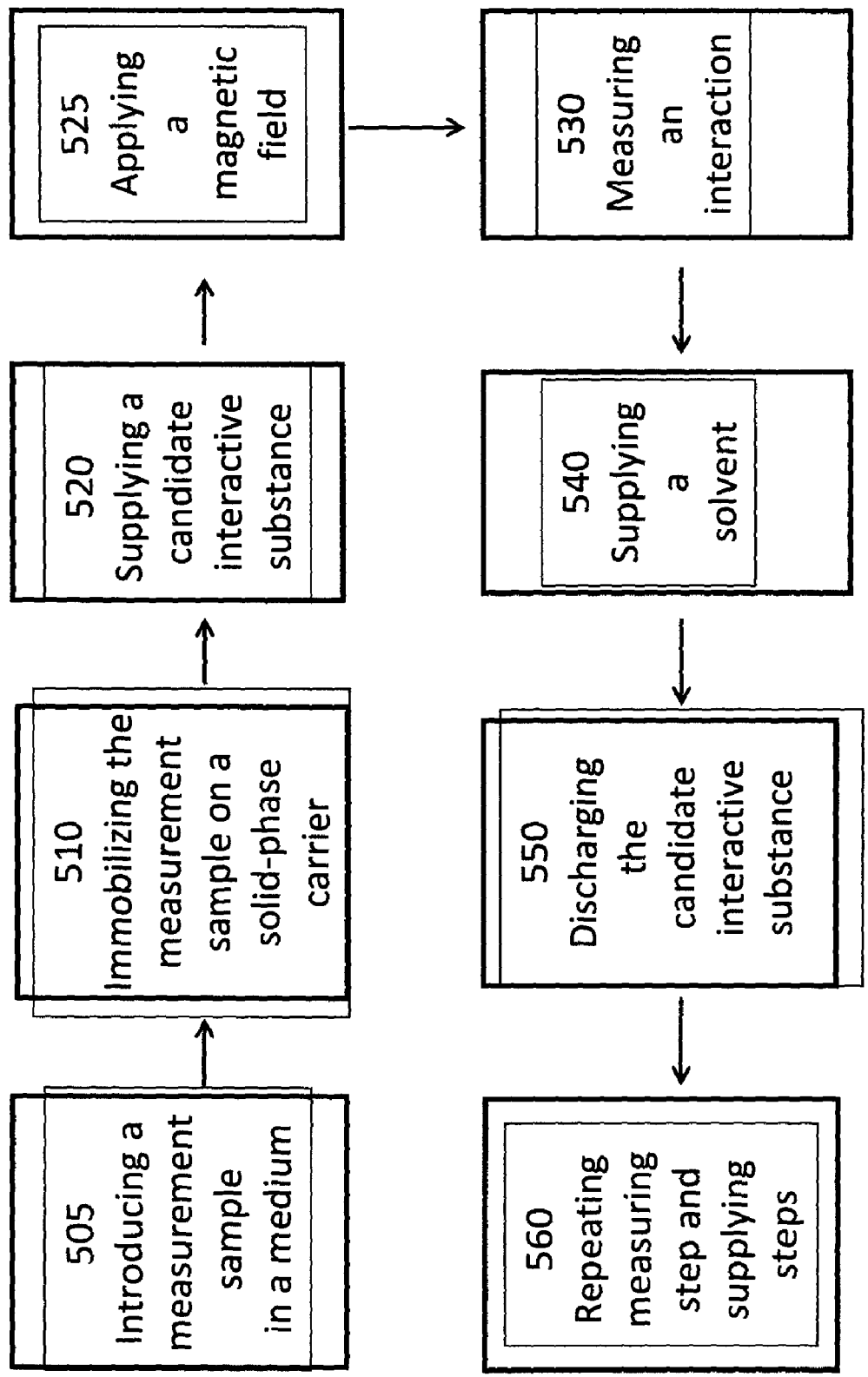
FIG. 7 is a diagram showing yet another example of various steps that can be performed in accordance with methods of the present invention.

101: a solution-introducing pipe
102: an analytical column
103: a solution-discharging pipe
115: packing
125: a solution NMR apparatus
135: an NMR measuring magnet
204: solid-phase carriers
205: a filter
305: introducing a measurement sample in a medium
310: immobilizing the measurement sample in the medium
315: applying a magnetic field
320: measuring the immobilized measurement sample by solution NMR
330: supplying a mobilizing solvent
340: measuring the mobilized measurement sample by solution NMR
350: comparing the measurements to determine site
405: introducing a measurement sample in a medium
410: immobilizing the measurement sample on a solid-phase carrier
415: applying a magnetic field
420: supplying solution containing factors
430: measuring the measurement sample by solution NMR
505: introducing a measurement sample in a medium
510: immobilizing the measurement sample on a solid-phase carrier
520: supplying a candidate interactive substance
525: applying a magnetic field
530: measuring an interaction
540: supplying a solvent
550: discharging the candidate interactive substance
560: repeating measuring step and supplying steps

The invention claimed is:

1. A method for high throughput screening candidate interactive substances comprising:
introducing a measurement sample in a medium into an analytical column;
immobilizing the measurement sample on a solid-phase carrier in the analytical column in an NMR-detecting cell;
supplying the immobilized measurement sample with a candidate interactive substance through a solution-introducing pipe;
applying a magnetic field to the NMR-detecting cell;
measuring the interaction between the measurement sample and the candidate interactive substance by solution NMR;
supplying a solvent capable of dissociating only the association between the measurement sample and the candidate interactive substance through the solution-introducing pipe to release the candidate interactive substance from the measurement sample;
discharging the candidate interactive substance from the NMR-detecting cell through a solution-discharging pipe; and
repeating the first supplying step, the measuring step, and the second supplying step.

2. The method according to claim 1, wherein the solid-phase carrier comprises at least one of a resin and a gel.

3. A method for carrying out solution NMR measurement in real time comprising:
introducing a measurement sample in a medium into an analytical column in a NMR-detecting cell;
immobilizing the measurement sample on a solid-phase carrier in the analytical column in the NMR-detecting cell;
applying a magnetic field to the NMR-detecting cell;
supplying a solution containing external environment-changing factors through a solution-introducing pipe in order to change consecutively the external environment around the immobilized measurement sample; and
measuring the measurement sample by solution NMR during the supplying step.

4. The method according to claim 3, wherein the measurement sample is a protein, and the measuring comprises tracing a midterm process toward a folding of the protein.

5. The method according to claim 3, wherein the solid-phase carrier comprises at least one of a resin and a gel.

6. A solution NMR apparatus comprising:
an analytical column having an introducing side and a discharging side, provided with filters on the introducing side and/or on the discharging side, and filled with a solid-phase carrier capable of immobilizing a measurement sample in a medium;
a solution-introducing pipe, operably associated with the introducing side, capable of supplying a solution for changing the external environment around the immobilized measurement sample or a candidate interactive substance;
a solution-discharging pipe, operably associated with the discharging side, capable of discharging the solution or the candidate interactive substance; and
a tube operably connectable to the solution-introducing pipe and the analytical column on the introducing side.

7. The solution NMR apparatus according to claim 6, wherein the tube comprises at least one filter and packing.

8. An NMR-detecting cell for a solution NMR apparatus comprising:
a solution-introducing pipe extending outside an NMR measuring magnet;
a solution-discharging pipe extending outside the NMR measuring magnet; and
an analytical column operably connectable to the solution-introducing pipe on an introducing side and the solution-discharging pipe on a discharging side, provided with filters on the introducing side and/or on the discharging side, and further filled with a solid-phase carrier.

9. A solution NMR apparatus comprising the NMR-detecting cell for a solution NMR apparatus according to claim 8.

10. The solution NMR apparatus according to claim 9, wherein the analytical column is detachable.

11. The NMR-detecting cell for a solution NMR apparatus according to claim 8, wherein the tube comprises at least one filter and packing.

12. A method for solution NMR-measuring comprising:
introducing a measurement sample in a medium into an analytical column,
immobilizing the measurement sample in the medium in an NMR-detecting cell
applying a magnetic field to the NMR-detecting cell; and
measuring the immobilized measurement sample by solution NMR under the condition that the external environment around the immobilized measurement sample is consecutively changing.

13. The method for solution NMR-measuring according to the preceding claim 12, wherein the measurement sample is immobilized by adsorbing on a solid-phase carrier.

14. The method for solution NMR-measuring according to claim 13, wherein the solid-phase carrier comprises at least one of a resin and a gel.

15. The method for solution NMR-measuring according to claim 12, wherein the change in the external environment is a change in the medium in which the immobilized measurement sample is present.

16. The method for solution NMR-measuring according to claim 12, wherein the change in the external environment is mediated by a solution-introducing pipe and a solution-discharging pipe of the NMR-detecting cell within the NMR-measuring magnet.

17. The method for solution NMR-measuring according to claim 12, further comprising:
supplying a solvent to the analytical column that is capable of mobilizing the measurement sample; and
measuring the mobilized measurement sample by solution NMR under the condition that the external environment around the mobilized measurement sample is consecutively changing; and
comparing the measurements to determine a site of the measurement sample that contributes to the immobilization.

* * * * *

SEQUENCE LISTING

```
<160> NUMBER OF SEQ ID NOS: 1

<210> SEQ ID NO 1
<211> LENGTH: 37
<212> TYPE: PRT
<213> ORGANISM: artificial sequence
<220> FEATURE:
<223> OTHER INFORMATION: linker between GST and calmodulin

<400> SEQUENCE: 1

Leu Val Pro Arg Gly Ser Ala Met Gly Gly Gly Gly Ser Gly Gly Gly
1               5                   10                  15

Gly Ser Gly Gly Gly Gly Ser Gly Gly Gly Gly Ser Leu Glu Val Leu
            20                  25                  30

Phe Gln Gly Pro His
        35
```